United States Patent [19]

Scarpa et al.

[11] Patent Number: 4,767,614

[45] Date of Patent: Aug. 30, 1988

[54] MODIFIED DEXTRANS IN A DENTAL HEALTH METHOD DEACTIVATING GLUCOSYLTRANSFERASE ENZYMES

[75] Inventors: Ioannis S. Scarpa, Chicago; Andrew M. Chludzinski, Westmont; Milan D. Janic, River Forest, all of Ill.

[73] Assignee: Wm. Wrigley Jr. Company, Chicago, Ill.

[21] Appl. No.: 942,961

[22] Filed: Dec. 16, 1986

Related U.S. Application Data

[63] Continuation of Ser. No. 584,824, Feb. 29, 1984, abandoned.

[51] Int. Cl.$^4$ .......................... A61K 9/68; A61K 7/16; A61K 31/73; A61K 31/735
[52] U.S. Cl. ...................................... 424/48; 424/49; 514/59; 536/112
[58] Field of Search ...................... 424/48, 49; 514/59; 536/112

[56] References Cited

U.S. PATENT DOCUMENTS

| | | | |
|---|---|---|---|
| 3,580,903 | 5/1971 | deBelder et al. | 536/112 |
| 4,228,150 | 10/1980 | Robyt | 424/48 |
| 4,335,100 | 6/1982 | Robyt | 424/48 |
| 4,335,102 | 6/1982 | Nakashima et al. | 424/48 |
| 4,340,673 | 7/1982 | Stoudt | 435/97 |
| 4,376,761 | 3/1983 | Okami | 424/48 |
| 4,430,322 | 2/1984 | Stoudt | 424/49 |

OTHER PUBLICATIONS

Sunstar, Inc., Cited in Chem. Abstracts vol. 94:109104d 1981.
Inoue, M. and Smith, E., "Specific Inhibition of Glucosyltransferase of *Streptococcus mutans*", *Carbohydrate Research*, vol. 80 pp. 163–177 (1980).
Ono, K., Nuessle, D. and Smith, E., "Oxidized Saccharides as Inhibitors of [alpha] Glucan Synthesis by *Streptococcus Mutans* Glucosyltransferase", *Carbohydrate Research*, vol. 88 pp. 119–134 (1981).
Tnaniyavarn, S. et al., "Kinetic Analysis for the Inhibition of Dextransucrase by Aminosugars" in Proceedings 'Glucosyltransferases, Glucans, Sucrose and Dental Caries' Editors: Doyle, R. J. and Ciardi, J. E. Sp. Supp. *Chemical Senses*, 1983; pp. 161–170 (1983).
Miyasaki, T. and Newbrun, E. "Inhibition of Adherence of *Streptococcus mutans* by Acarbose", in Proceedings 'Glucosyltransferases, Glucans, Sucrose and Dental Caries' Editors: Doyle, R. J. and Ciardi, J. E. Sp. Supp. *Chemical Senses*, 1983; pp. 201–210 (1983).
Kobayashi, K. and Sumitomo, H. "Synthesis of Partially 3-deoxygenated (1,6)-a-D-glucopyranan" *Carbohydrate Research* vol. 115 (1983) pp. 243–249.
Toshiyuki, U., et al., "Chemical Synthesis of Amino--Group-Containing (1,6)-a-D Glucan Derivatives by Ring-Opening Polymerization of 1,6-Anhydro Azido Sugars", *Macromolecules* vol. 16 (1983) pp. 853–858.
deBelder, A. N., et al., "Synthesis of Ketodextrans", *Acta Chemica Scandinavica*, vol. 22 (1968) pp. 949–952.

*Primary Examiner*—Ronald W. Griffin
*Assistant Examiner*—Jacqueline M. Stone
*Attorney, Agent, or Firm*—Willian Brinks Olds Hofer Gilson & Lione Ltd.

[57] ABSTRACT

The compounds of the present invention are linear and branched dextrans having a plurality of their glucose units modified at the 3-position ring carbon with groups selected from the class consisting of keto, amino, halo, benzyl, alkyl, sulfonyl, carboxyl and hydrogen. The modified dextrans reduce and/or modify activity of glucosyltransferase enzymes (GTF) which are produced by oral strains of *Streptococcus mutans* bacteria. GTF enzymes mediate oral biosynthesis of plaque-forming glucose polymers (glucans) from ingested sucrose. Therefore, the dextrans of the present invention, which reduce and/or modify activity of GTF enzymes, are useful in reducing the formation of dental plaque. The present invention is further directed to a dental health method comprising the step of contacting the oral cavity with linear or branched dextran compounds having a plurality of their glucose units modified at the 3-position carbon with a group such as keto, amino, halo, benzyl, alkyl, sulfonyl, carboxyl or hydrogen.

22 Claims, 5 Drawing Sheets

Branched (Natural) Dextran or Glucan

FIG. 3

Aminated Dextran (3-aminodextran) Axial

Aminated Dextran (3-aminodextran) Equatorial

MODIFIED DEXTRANS IN A DENTAL HEALTH METHOD DEACTIVATING GLUCOSYLTRANSFERASE ENZYMES

This application is a continuation of application Ser. No. 584,824, filed Feb. 29, 1984, now abandoned.

BACKGROUND OF THE INVENTION

1. Field of the Invention

The present invention is directed to a dental health composition and method for reducing the onset of dental caries and plaque-associated periodontal disease. More particularly, the invention involves a group of modified dextrans which reduce dental plaque formation by reducing and/or modifying the activity of plaque-producing glucosyltransferase (GTF) enzymes secreted by bacteria in the mouth.

2. Description of the Prior Art

The term "GTF" is used to abbreviate a group of extracellular glucosyltransferase enzymes elaborated by numerous strains of cariogenic *Streptococcus Mutans* bacteria which are known to inhabit the oral environment, multiplying on the teeth and gums. The bacteria-produced enzymes rapidly convert ingested sucrose into large polymers of glucose, called glucans or dextrans, which adhere to tooth enamel and other oral surfaces including dental appliances.

As is well-known in the art, the gradual accumulation of glucans on oral surfaces results in a film of sticky dental plaque if left untreated. Plaque causes dental caries and related periodontal disorders because it provides a protective matrix within which cariogenic *S. Mutans* bacteria will readily colonize. Plaque also causes agglomeration of food debris on dental surfaces and prevents salivary neutralization of harmful lactic acid secreted by bacterial cells lodged in the plaque matrix. Despite efforts to counteract plaque with ordinary hygiene measures such as brushing and flossing, plaque deposition in many instances will still result in the gradual appearance of carious lesions in the teeth. Such lesions occur when tooth enamel is dissolved by lactic acid secreted into the plaque matrix as a by-product of metabolic processes on-going in plaque-bound bacterial cells.

Glucan molecules, the principal component of dental plaque, are enormous soluble and insoluble polymers of glucose having molecular weights as high as $10^6$. By a mechanism postulated in Robyt, et al., *Arch. Biochem. Biophys.*, Volume 165, p. 634 (1974), glucose units obtained from dietary sucrose are converted by GTF enzymes into polymers of glucose called dextrans, many of which, after sufficient lenghtening and branching, exhibit properties of insolubility and adhesiveness characteristic of high molecular-weight plaque glucans. Although the GTF-mediated synthesis of glucans can begin with a single glucose unit, the rate of polymer enlargement will increase only gradually and then level off when the molecule has reached a molecular weight of approximately 6,000. However, this slow initial growth phase can be accelerated if, instead of single glucose units, low molecular-weight dextrans are provided as the starting material for the GTF reaction. These smaller glucose polymers are commonly referred to as dextran primers.

The mechanism of GTF-catalyzed glucan synthesis and the phenomenon that dextrans act as primers for GTF synthesis of plaque glucans have led to investigation whether certain chemically modified dextrans might exhibit an opposite effect upon the GTF reaction, namely, a reduction of glucan synthesis by attachment to the GTF enzyme binding site to form an enzyme/modified primer complex which appreciably slows down further glucan synthesis. The expected utility of such hypothetical blocking compounds can be readily appreciated when contrasted with present anti-caries, anti-plaque hygienic measures such as tooth-brushing and fluoride rinses which attempt with only marginal success to eradicate existing plaque and bacterial build-up.

Robyt et al., U.S. Pat. No. 4,228,150 disclosed that fluorosucroses substituted with fluorine for at least the $C_6$ hydroxyl group of sucrose (and possibly other hydroxyls) inhibited GTF synthesis of dextran from sucrose. Robyt et al., U.S. Pat. No. 4,335,100 further disclosed a method for inhibiting GTF enzyme involving use of substituted sucrose compounds having an inhibiting group bonded to the 5'-position ring carbon. The inhibiting group was one of the following groups: $-CH_2X$, $=CH_2$, $-CHO$, or H (wherein X is selected from the class consisting of $-Cl$, $-Br$, I, $-N_3$, $-NH_2$, $-OCH_3$, or $-H$).

Thaniyavarn, S. et al, "Kinetic Analysis for the Inhibition of Dextransucrase by Aminosugars" in Proceedings 'Glucosyltransferases, Glucans, Sucrose and Dental Caries' Editors: Doyle, R. J. and Ciardi, J. E. Sp. Supp. *Chemical Senses*, 1983; pp. 161-170 (1983), disclosed that the sugars 6,6'-diamino-6,6'-dideoxysucrose, 6'-amino-6'deoxysucrose, 6-amino-6-deoxysucrose, and 6-amino-6-deoxymethyl-a-D-glucopyranoside, are inhibitors of the enzyme dextransucrase.

Miyasaki, T. and Newbrun, E. "Inhibition of Adherence of Streptococcus mutans by Acarbose", in Proceedings 'Glucosyltransferases, Glucans, Sucrose and Dental Caries' Editors: Doyle, R. J. and Ciardi, J. E. Sp. Supp. *Chemical Senses*, 1983; pp. 201-210 (1983), disclosed that the pseudotetrasaccharide consisting of the seven-carbon cyclitol unit linked to the amino group of 4-amino-4,6-dideoxyglucose which, in turn, is in alpha 1,4 linkage to a maltose disaccharide, inhibits synthesis of water-insoluble glucans by glucosyltransferase enzyme.

Other research to identify GTF inhibitors involved modification of dextran through partial periodate oxidation.

See Inoue et al., *Carbohydrate Research*, Volume 80, pp. 163-177 (1980). Inoue et al. disclosed that commercially available branched dextran, when modified by an oxidative scission of covalent bonds between carbon atoms 2 and 3 in an undetermined percentage of glucose units in the dextran, exhibited potent in-vitro GTF-deactivation. GTF inhibition by the oxidized dextran was postulated to result from an interaction between 2,3-dialdehyde groups present in the partially oxidized dextran and reactive functional groups close to the dextran binding site of the GTF enzyme.

The most recently disclosed GTF inhibitor known by applicant is the compound homocitric acid oligoriboside as claimed in Okami et al., U.S. Pat. No. 4,376,761.

SUMMARY OF THE INVENTION

The present invention is directed to a group of dextran compounds and also to a method of utilizing such compounds to reduce and/or modify GTF-mediated glucan synthesis and bring about a consequent reduction in plaque formation on dental surfaces.

In its composition aspect, the present invention generically includes a group of linear and branched dextran compounds having a plurality of their glucose units modified at the 3-position carbon. More specifically, the compounds of the present invention are: (a) a linear dextran consisting of glucose units joined essentially by alpha 1,6 glycosidic linkages, wherein a plurality of the units are modified at the 3-position ring carbon by replacement of 3-position —OH groups with a group selected from the class consisting of halo, benzyl, alkyl, sulfonyl and carboxyl; (b) a linear dextran consisting of glucose units joined essentially by alpha 1,6 glycosidic linkages, wherein a plurality of the units are modified at the 3-position carbon by replacement of 3-position —H and —OH groups with a keto group; and (c) a branched dextran consisting of glucose units joined by alpha 1,6 and branched by alpha 1,3 glycosidic linkages, wherein a plurality of the units are modified at the 3-position carbon by replacement of 3-position —OH groups with a group selected from the class consisting of amino, halo, benzyl, alkyl, sulfonyl, carboxyl and hydrogen.

In its method aspect, the present invention is directed to plaque reduction by topical application to the oral cavity (preferably by way of a gradual release medium such as chewing gum) of linear or branched dextran compounds consisting of glucose units wherein a plurality of the units are modified at the 3-position ring carbon by (a) replacement of 3-position —OH groups with groups such as amino, halo benzyl, alkyl, sulfonyl, carboxyl and hydrogen; or (b) replacement of 3-position —H and —OH groups with a group such as a keto (=O) group.

Branched or linear dextrans may be used as starting reagents for preparation of the dental health compounds of the present invention. However, with respect to certain dextrans of the present invention, it has been found that the linear modified dextran results in greater reduction of GTF activity than the similarly modified branched compound.

DESCRIPTION OF THE INVENTION

The modified dextrans of the present invention bring about a reduction, in-vitro, of GTF-mediated synthesis of high molecular-weight plaque glucans from sucrose. As is well known, enzyme-produced glucans enhance deposition of bacteria on dental surfaces and thereby establish an environment favorable to the onset of dental caries and plaque-associated periodontal disease. The use of the modified linear and branched dextrans according to the present invention reduces glucan production by reducing the catalytic activity of GTF enzymes.

In addition to reducing the production of glucans by GTF, the glucan polymers which are produced in the presence of the modified primers of the present invention have less tendency to cause an agglomeration of bacteria than the glucans normally synthesized by GTF. Thus plaque accumulation on oral surfaces may be reduced by the removal of such low-adherence glucans and bacteria by saliva and/or normal oral hygiene measures.

We hypothesize that this reduction in adherence results from a modification of the enzymatic glucan synthesis such that the glucans produced are less branched and/or are of lower molecular weight. These differences would result in lower adhesion and/or increased water solubility of the glucans. The ability to reduce and/or modify glucan synthesis renders the compounds of the present invention effective for reducing dental plaque formation.

Figures 2, 3:
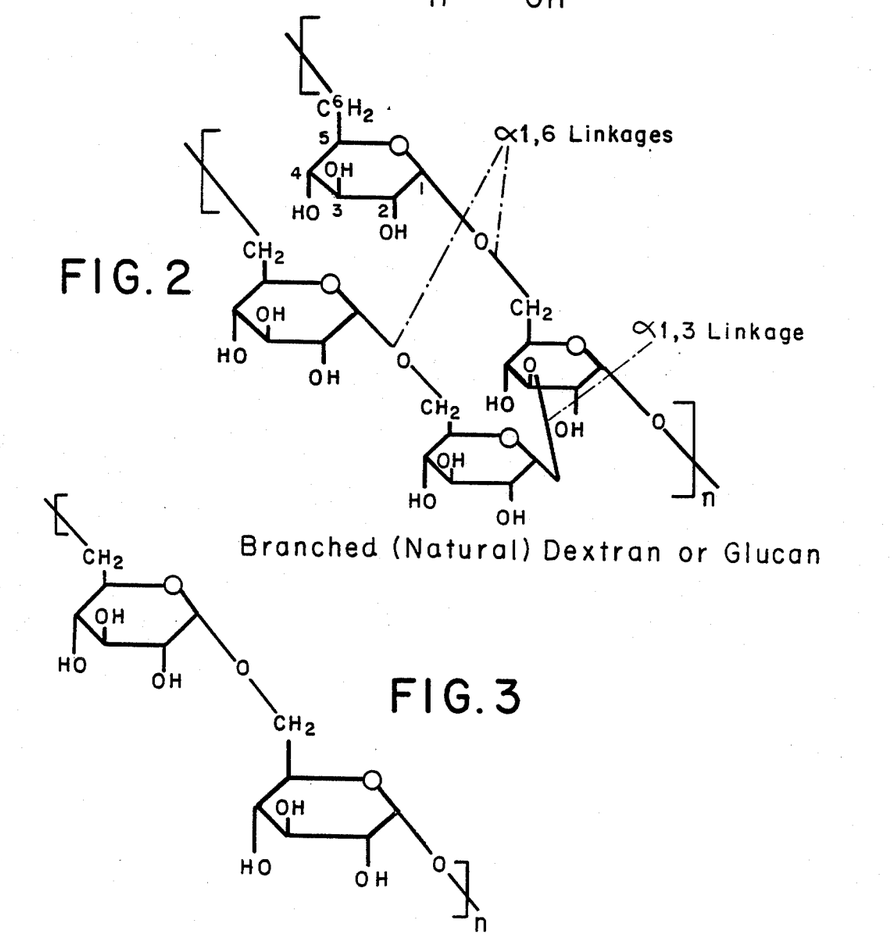
FIG. 2 is a structural representation of naturally-occurring branched (alpha 1,6-alpha 1,3) dextran.
FIG. 3 is a structural representation of synthetic linear (alpha 1,6) dextran.
Figure 8:
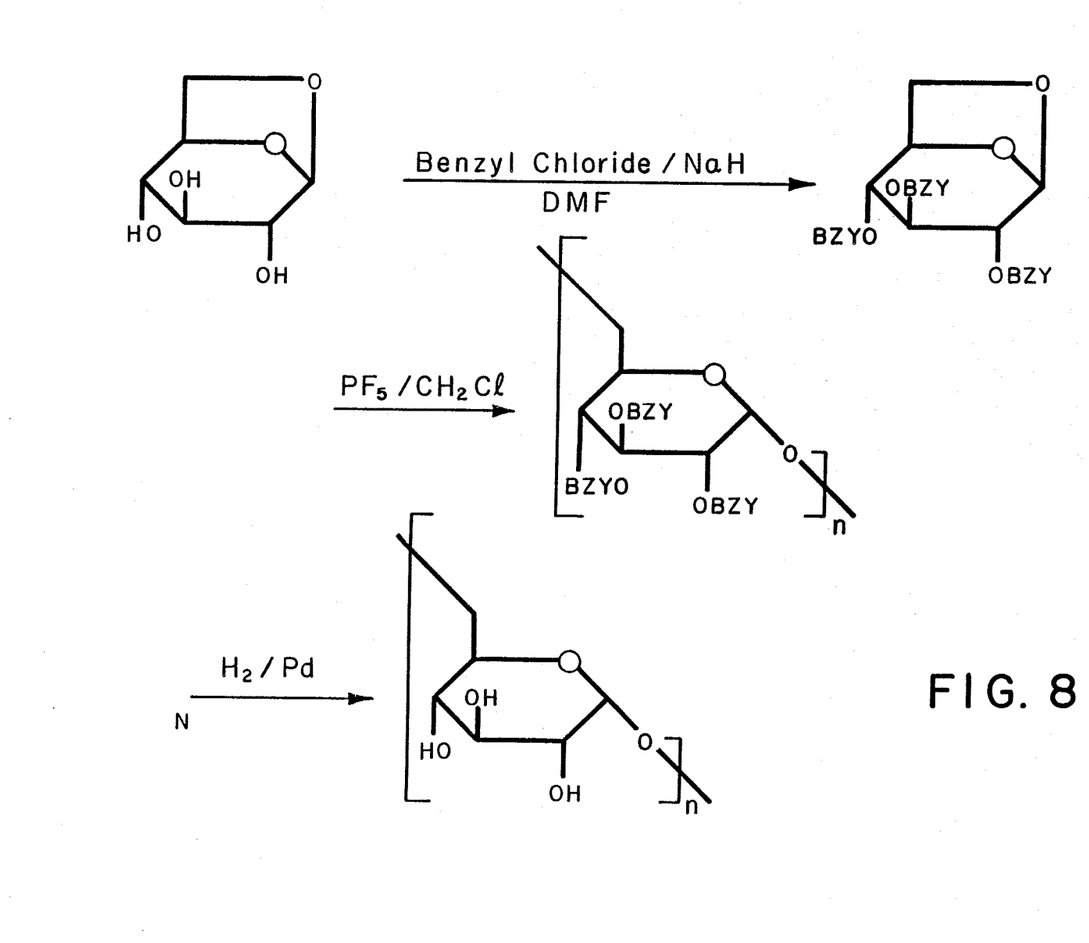
FIG. 8 is a structural representation of the synthesis of linear dextran from levoglucosan.

Chemically, dextrans are polymers of glucose similar to the plaque glucans manufactured by GTF enzyme but differing in that dextran is a much smaller, less branched polymer than glucan. Dextran may be purchased in a naturally occurring branched form (commercially identified as T-10 dextran) in which repeating glucose units are joined by alpha 1,6 and branched by alpha 1,3 glycosidic linkages. (see FIG. 2) A synthetic linear dextran (FIG. 3) containing only alpha 1,6 linkages is not commercially available but may be prepared in the laboratory from the substance levoglucosan in accordance with a known chemical synthesis (FIG. 8) which is described in Example 1 below.

Throughout the present disclosure the term "linear dextran" will be understood by those skilled in the art as referring to a dextran compound consisting of glucose units joined essentially by alpha 1,6 glycosidic linkages, while the term "branched dextran" will be understood as referring to a dextran compound in which the glucose units are joined by alpha 1,6 and branched by alpha 1,3 glycosidic linkages.

The chemical group names or prefixes keto, amino, halo, benzyl, alkyl, sulfonyl, carboxyl and hydrogen as used herein to characterize the modified dextrans of the present invention will be understood by those skilled in the art as denoting the following functional groups: keto (=O); amino (—NH$_2$); halo (—Cl,—Br,—F and —I); benzyl (C$_6$H$_5$(CH$_2$)); alkyl (—CH$_3$, —CH$_2$CH$_3$, . . . —(CH$_2$)$_n$CH$_3$, —CH(CH$_3$)$_2$, and —C(CH$_3$)$_3$); sulfonyl (—SO$_3$H); carboxyl (—COOH); and hydrogen (—H).

Specifically, the compounds claimed in the present invention are as follows: linear 3-ketodextran, linear 3-halodextran, linear 3-benzyldextran, linear 3-alkyldextran, linear 3-sulfonyldextran, linear 3-carboxyldextran, branched 3-aminodextran, branched 3-halodextran, branched 3-benzyldextran, branched 3-alkyldextran, branched 3-carboxyldextran and branched 3-dehydroxydextran.

Figure 1:
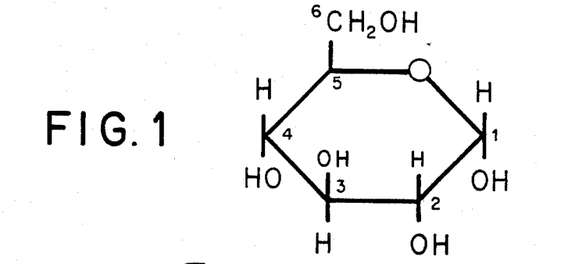
FIG. 1 is a Haworth structure showing the carbon numbering system for glucose.

The '3' prefix in the above listed compounds signifies that a plurality of the glucose units making up the dextrans are modified at the 3-position carbon by either replacement of 3-position —H and —OH groups with a single double-bonded group (as in the case of 3-ketodextran) or by replacement of 3-position —OH groups (as in the case of 3-amino-, 3-halo-, 3-benzyl-, 3-alkyl-, 3-sulfonyl-, 3-carboxyl-, and 3-dehydroxydextran). The numbering system for glucose carbons is shown in the Haworth structure of FIG. 1.

The dental health method of the present invention involves a topical application to the oral cavity of linear or branched dextrans having a plurality of their glucose units modified at the 3-position ring carbon by replacement of one or both of the groups —H and —OH present at that carbon position with a group such as keto (=O replacing both —H and —OH) or groups such as amino, halo, benzyl, alkyl, sulfonyl, carboxyl and hydrogen (replacing —OH).

It will be readily understood by those skilled in the art that the above modified dextrans may be synthesized using known chemical procedures which leave intact the ring structure of glucose units in the dextran reagents, as distinguished from the ring-opening periodate oxidation of dextran disclosed in Inoue et al. (cited above).

Figure 5:
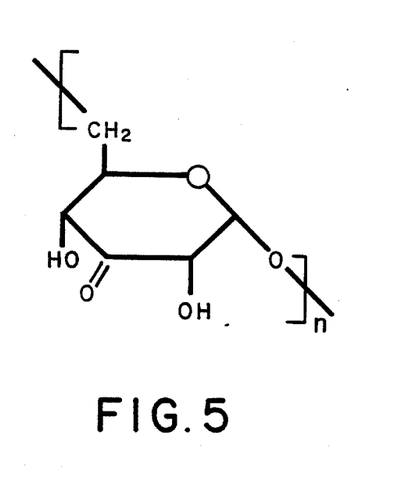
FIG. 5 is a structural representation of 3-ketodextran.
Figure 6:
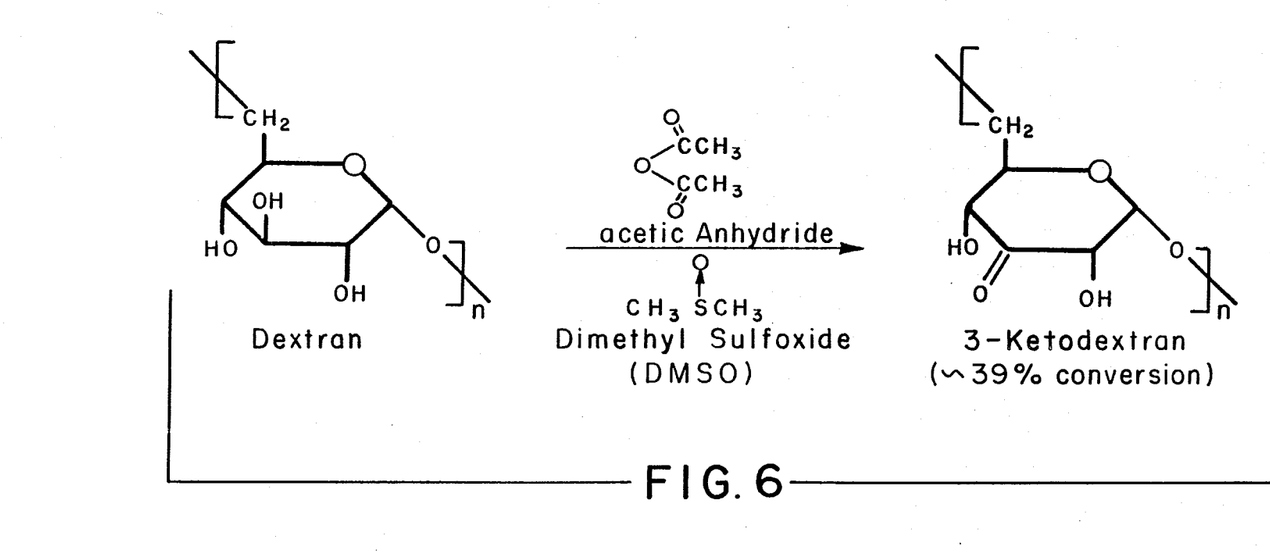
FIG. 6 is a structural representation of the synthesis of 3-ketodextran from dextran.

For example, 3-ketodextran (FIG. 5) may be prepared from either linear or branched dextran by using a known chemical reaction to oxidize some of the 3-position hydroxyl groups of individual dextran units to carbonyls. Specifically, this conversion may be carried out in accordance with Lindberg, *Acta Chemica Scandinavica* Vol. 13, pp. 1226–1230 (1959) and DeBelder, A. N., Lindberg, B., and Svensson, S. *Acta Chemica Scandinavica* Vol. 22, pp. 949–952 (1968). The oxidation reaction, which is depicted in FIG. 6 of the drawings, results essentially in 3-keto conversion in approximately 39% of the glucose units making up the dextran reactants.

Figure 4:
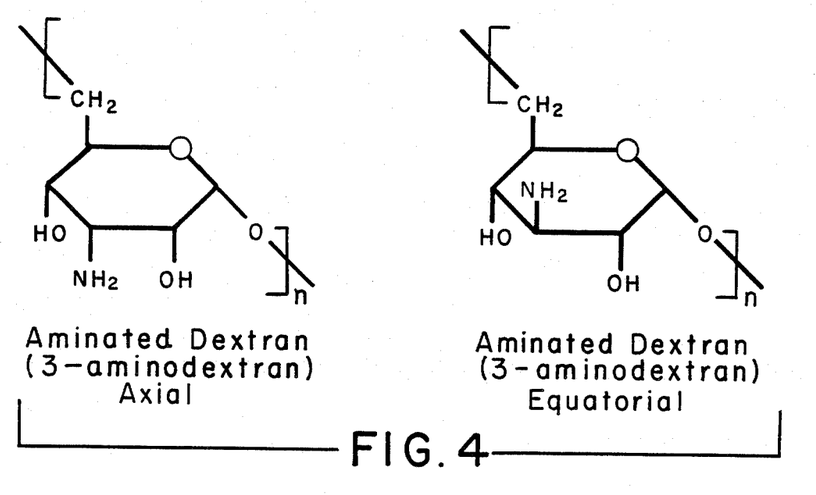
FIG. 4 is a structural representation of 3-aminodextran.
Figure 7:
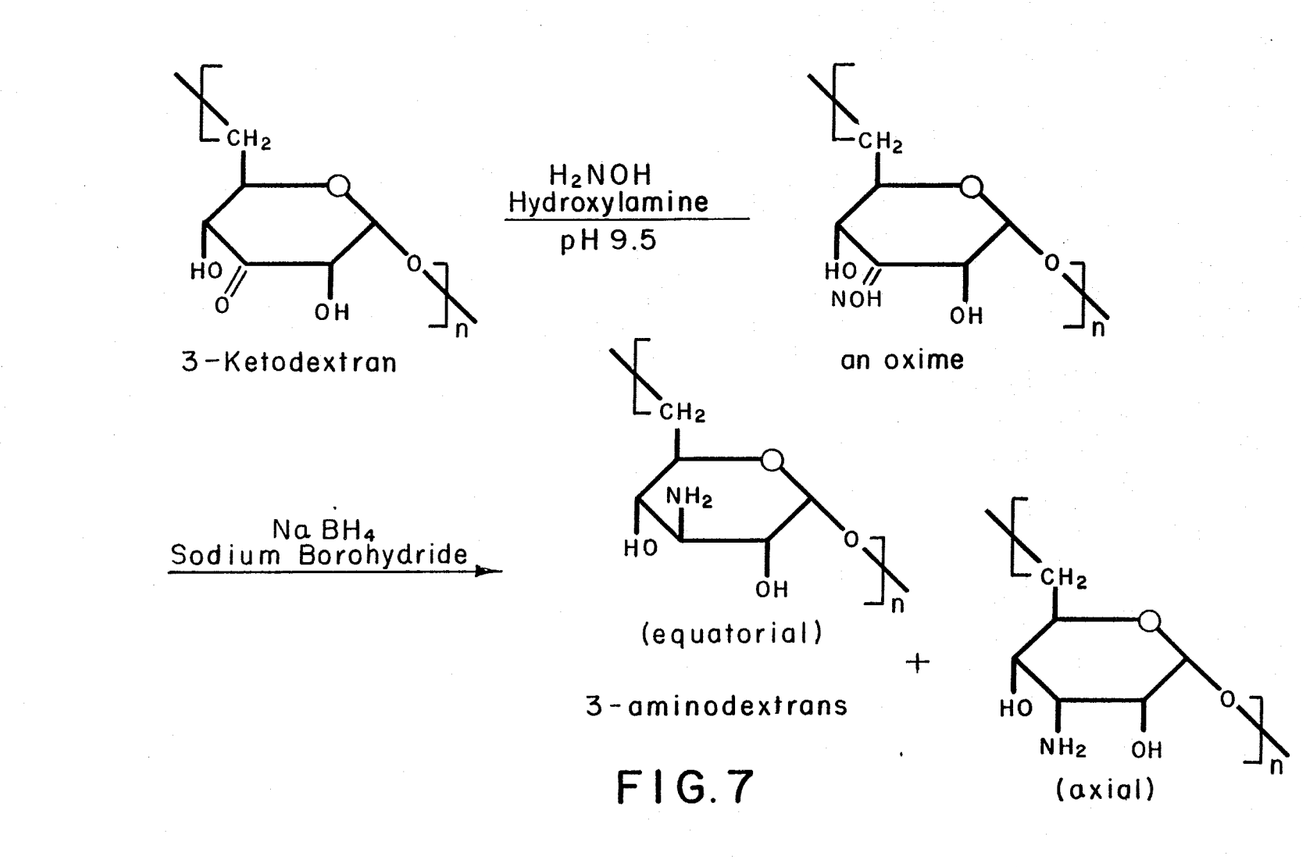
FIG. 7 is a structural representation of the synthesis of 3-aminodextran from 3-ketodextran.

A further plaque reducing compound of the present invention is 3-aminodextran (FIG. 4) which may be prepared using a conventional chemical synthesis to bond amino groups to the 3-position ring carbons of individual glucose units in branched or unbranched dextrans. Such a conversion (see FIG. 7) requires as a starting reagent the branched or linear 3-ketodextran synthesized as generally described above. Briefly, the amino conversion involves a condensation reaction of the carbonyl group of 3-ketodextran with hydroxylamine carried out under basic conditions. Hydroxylamine converts 3-ketodextran to the corresponding 3-oxime which is then reduced with sodium borohydride to convert the oxime group (=NOH) to the desired amino group (—NH$_2$) at the 3-position ring carbon of glucose units in the dextrans.

One particular aspect of the invention should be noted here, namely, that linear 3-ketodextran has been found to exhibit more potent reduction of GTF activity than its branched counterpart. As linear dextran is not commercially obtainable, a preliminary synthesis of the linear compound, as described in Example 1 below, becomes necessary for the preparation of a 3-ketodextran capable of maximum reduction of plaque synthesis.

The preparation of 3-ketodextran and 3-aminodextran is described in further detail in the following examples.

EXAMPLE 1

3-Ketodextran

Step 1: Preparation of Linear Dextran. In accordance with the methods described in Wolff, I. A., Olds, D. W., and Hilbert, G. E., *Die Staerke*, Volume 20 pp. 150–158 (1968) and Shuerch C. and Ruckel, E. R., *Journal of the American Chemical Society*, Volume 31 pp. 2233–2239 (1966), a linear (alpha 1-6) dextran may be prepared from levoglucosan according to the following procedures.

a. Synthesis of Levoglucosan. Soluble potato or corn starch is transformed into crystalline lumps. These lumps are pyrolized and a syrup is formed which crystallizes on standing. The resulting crude levoglucosan is further purified by a standard acetylation procedure. Acetylated levoglucosan is distilled in vacuo and deacetylated with sodium methoxide in anhydrous methanol. After three recrystallizations from absolute ethanol, pure levoglucosan melts at 177°–179.5° C.

b. Polymerization of Levoglucosan. Prior to polymerization, hydroxy groups of levoglucosan are protected by etherification with benzyl- or xylyl chloride and sodium hydride in anhydrous dimethyl formamide. Perbenzylated levoglucosan is purified by crystallization from absolute ethanol (three times) and then from hexane/methylene chloride, to remove any traces of ethanol which could prevent the subsequent polymerization.

Perbenzylated levoglucosan is then polymerized in methylene chloride at low temperature (—73° to —75° C.), in the absence of air and moisture, using PF$_5$ as an initiator. Phosphorus pentafluoride is generated by pyrolytic decomposition of p-chlorobenzene diazonium phosphorus hexafluoride. The polymerization reaction is stopped with cold anhydrous methanol. The polymer is isolated from the solution after dilution with methylene chloride, and washing of the organic phase with aqueous bicarbonate solution, water and brine. Washed solution is dried over anhydrous sodium sulfate and magnesium sulfate. Polymer is isolated by pouring the dried solution into an excess of a mixture of hexane-benzene (3:1). Precipitated polymer is dried in vacuo to constant weight and re-precipitated from methylene chloride solution using a mixture of hexane-chloroform (6:1). The re-precipitated polymer should not contain any detectable amounts of monomer.

The resulting per-benzylated synthetic polyglucan is dissolved in N-methyl pyrrolidone containing 8% (V/V) water. Palladium acetate is dissolved separately in the same solvent and both solutions are purged with argon to remove oxygen. The solutions are mixed together, then placed in a water bath at 40° C. with hydrogen gas introduced at atmospheric pressure. The mixture turns black after a few minutes and the reaction is continued for six hours during which time debenzylation is completed. The mixture is diluted with 5% (w/v) aqueous sodium chloride and refrigerated overnight. Coagulated palladium is separated by filtration and washed with water. The filtrate is combined with the washings, dialyzed extensively against deionized water, and freeze-dried. The white fluffy product is very hygroscopic requiring storage in a desiccator. The molecular weight of the final linear dextran is estimated by intrinsic viscosity to be in the range of 10,000 to 30,000.

Step 2: Conversion of Dextran to 3-ketodextran. The linear dextran prepared in accordance with Step 2, above, or a commercially obtained natural branched dextran, is dried for 100 hours at 50° C., 0.1 torr, and dissolved in dry dimethyl sulfoxide (DMSO). Acetic anhydride is added to the stirred solution and stirring should continue for two hours at 40° C. The clear, slightly yellowish solution is poured into an excess of water, stirred for 15 minutes and dialysed for four days against deionized water. The freeze-dried product is hygroscopic.

EXAMPLE 2

3-Aminodextrans

Step 1: Preparation of Linear Dextran. (See Step 1 of Example 1 above.)

Step 2: Preparation of 3-aminodextran. The starting reactant for making the 3-aminodextran of the present invention is the linear (or branched) 3-ketodextran prepared in Example 1, above. To prepare the aminodextran, the 3-ketodextran is first converted to the 3-oxime derivative by suspending the 3-ketodextran in a solution of hydroxylamine chlorohydrate in a 1:1 ethanol-pyridine mixture (V/V). The mixture is shaken for 2 hours at room temperature during which time dextran completely dissolves. To the resulting oxime solution is then added a 1:1 solution (V/V) of ethanol and pyridine, the solution containing dissolved sodium borohydride. The mixture is shaken for two hours at room temperature and left overnight. Crude product is dissolved in deionized water acidified with HCl to pH 2. The acid is neutralized after two minutes by adding phosphate buffer (pH 10). After dialysis against deionized water for fours days, the product is isolated by freeze-drying.

We claim:

1. A method for reducing dental plaque formation comprising the step of contacting the oral cavity with a dextran compound consisting of glucose units, a plurality of which are modified at the 3-position ring carbon thereof by replacement of the 3-position —OH group with a group selected from the class consisting of amino, halo, benzyl, alkyl, sulfonyl, carboxyl and hydrogen, while leaving the ring of the glucose unit intact.

2. The method of claim 1 wherein essentially all the glucose units are joined by alpha 1,6 glycosidic linkages such that the dextran has a linear structure.

3. The method of claim 1 wherein the group is amino.

4. The method of claim 1 wherein the group is benzyl.

5. The method of claim 1 wherein the group is alkyl.

6. The method of claim 5 wherein the alkyl group is methyl.

7. The method of claim 5 wherein the alkyl group is ethyl.

8. The method of claim 5 wherein the alkyl group is isopropyl.

9. The method of claim 5 wherein the alkyl group is t-butyl.

10. The method of claim 1 wherein the group is sulfonyl.

11. The method of claim 1 wherein the group is carboxyl.

12. The method of claim 1 wherein the group is hydrogen.

13. The method of claim 1 wherein the group is halo.

14. The method of claim 1 wherein the dextran is present in a chewing gum composition.

15. The method of claim 1 wherein the number of modified glucose units in the dextran is approximately 39% of the total number of glucose units.

16. The method of claim 1 wherein the modified dextran has a molecular weight in the range of from about 10,000 to about 30,000.

17. A method for reducing dental plaque formation comprising the step of contacting the oral cavity with a dextran compound consisting of glucose units, a plurality of which are modified at the 3-position ring carbon thereof by replacement of the 3-position —OH group and the 3-position —H group with a keto group, while leaving the ring of the glucose unit intact.

18. The method of claim 17 wherein essentially all the glucose units are joined by alpha 1,6 glycosidic linkages such that the dextran has a linear structure.

19. The method of claim 17 wherein the number of modified glucose units in the dextran in approximately 39% of the total number of glucose units.

20. The method of claim 17 wherein the dextran is present in a chewing gum composition.

21. The method of claim 18 wherein the dextran is present in a chewing gum composition.

22. The method of claim 19 wherein the dextran is present in a chewing gum composition.

* * * * *

UNITED STATES PATENT AND TRADEMARK OFFICE
CERTIFICATE OF CORRECTION

PATENT NO. : 4,767,614
DATED : August 30, 1988
INVENTOR(S) : Ioannis S. Scarpa et al.

It is certified that error appears in the above-identified patent and that said Letters Patent is hereby corrected as shown below:

On the cover page, in the name of the invention, after "METHOD" please insert --FOR--.

IN EXAMPLE I

In column 5, line 67, please delete "foIIowing" and substitute therefor --following--.

IN THE CLAIMS

In column 8, line 33, please delete the second occurrence of "in" and substitute therefor --is--.

Signed and Sealed this

Eighth Day of October, 1991

Attest:

HARRY F. MANBECK, JR.

*Attesting Officer*     *Commissioner of Patents and Trademarks*